United States Patent [19]

Solheim

[11] 4,062,222
[45] Dec. 13, 1977

[54] GOLF CLUB SWINGING APPARATUS

[76] Inventor: Karsten Solheim, 501 N. Wakanda Lane, Phoenix, Ariz. 85023

[21] Appl. No.: 741,219

[22] Filed: Nov. 12, 1976

[51] Int. Cl.² .............................................. G01N 3/00
[52] U.S. Cl. ................................... 73/13; 73/432 SD
[58] Field of Search ............. 73/432 SD, 13; 35/29 A

[56] References Cited

U.S. PATENT DOCUMENTS

| | | | |
|---|---|---|---|
| 1,703,507 | 2/1929 | Barnhart | 73/100 |
| 3,444,729 | 5/1969 | Shubert | 73/13; 73/13 X |
| 3,855,842 | 12/1974 | Imabori et al. | 73/13 |

FOREIGN PATENT DOCUMENTS

| | | | |
|---|---|---|---|
| 320,049 | 9/1929 | United Kingdom | 73/13 |

*Primary Examiner*—Charles A. Ruehl

*Attorney, Agent, or Firm*—Lindenberg, Freilich, Wasserman, Rosen & Fernandez

[57] ABSTRACT

A golf-club and golf-ball testing apparatus, having a crank arm driven by a main drive shaft, drives a club swinging arm through a secondary drive shaft supported by bearings on the end of the crank arm and turned by a planetary gear which meshes with teeth in a fixed gear concentric with the main drive shaft. The club swinging arm is connected to the secondary drive shaft by a short block, and the club is connected to the end of the swinging arm by a gripping member that is caused to rotate from an adjustable initial position so that the shaft is rolled through about 180° during a full swing. The short block is coupled to the secondary drive shaft by resilient material to absorb shocks between the swinging arm and the crank arm.

12 Claims, 16 Drawing Figures

GOLF CLUB SWINGING APPARATUS

BACKGROUND OF THE INVENTION

The present invention relates to golf-club and golf-ball testing apparatus, and more particularly to an apparatus for mechanically swinging a golf club for the purpose of testing the club or the ball.

The problems in testing golf clubs are significantly more involved than in testing golf balls. In the case of testing the latter, it would be sufficient to devise a mechanism for impacting a ball with a mallet using energy calculated to produce a predetermined initial velocity. To test golf clubs, however, it is desirable to control motion of the club from the top of the back swing to impact and beyond to follow through in a manner more nearly duplicating the motion that would be produced by a golfer.

Nearly every golfer has a different swing because of individual factors that vary from person to person, such as height, arm length, strength and the like. It would therefore not be practical to devise a mechanism for swinging a golf club that duplicates the swing of a particular person. However, it is important that a typical or average golfer be duplicated in order to truly test features of golf clubs, such as head or shaft design. Otherwise a tendency for the golf club to slice or hook the ball under normal golfing conditions may not be detected. In attempting to duplicate a normal swing of a golfer, it must be understood that the normal swing is not one which produces motion of the club head in a perfect circle like a spinning wheel, although it is helpful for golfers to visualize that swing pattern. Consequently, in devising a golf club swinging apparatus, it is not sufficient for the machine to swing the club about a fixed axis like a spoke in a wheel.

In visualizing the perfect swing to be like a spoked wheel spinning in a fixed plane at an acute angle with the ground, one fails to account for the fact that the center of the swing is not the center of the golfer's chest. It is instead more nearly at the leading shoulder of the golfer. The leading shoulder is that nearest the green, namely the left shoulder in the case of the right handed golfer. That center (shoulder point) is not fixed in space during the course of a normal swing, although the golfer strives to keep his head fixed in space, while virtually all of his body moves during the course of the swing. First it moves away from the target during the back swing. To raise the golf club up, back and around in the back swing, the leading shoulder dips below the center of the golfer's chest and moves closer to that center. Then during the down swing, the leading shoulder retraces its path and during the follow through rises above and closer to the center of the golfer's chest. All through the swing, the golfer not only pivots the golf club about his wrists but also rolls the club shaft such that, during the back swing, the club head moves further back away from a position normal to the direction of motion as the golfer cocks his wrists until, at the top of the back swing, the shaft has been rolled through about 90°. During the down swing, the shaft is rolled back as the wrists are uncocked. During the follow through the golfer continues to roll the club shaft through another 90°, more or less, as he cocks his wrists to break the swing.

If the golfer is consistent in his swing, he can quickly determine for himself how he should address the ball in order for the club head to be seemingly square at the moment of impact. For example, if there is a tendency to slice, the club head is apparently open (rotated back) at the moment of impact. The golfer compensates by addressing the ball with the club head initially closed. to be able to accomplish the same thing with precision for testing a golf club design, i.e., to be able to open or close the club head to a desired fine degree in addressing the ball, it would be desirable to not only be able to duplicate the rolling motion of the golfer's wrists but to also be able to initially open or close the club head before starting the down swing, usually while addressing the ball before starting the back swing.

OBJECTS AND SUMMARY OF THE INVENTION

An object of this invention is to provide a mechanism for swinging a golf club using a motion which takes into account the fact that the normal swing is not about a fixed point. Another object is to take into account the fact that the club is not pivoted by wrist action at a point on the axis of the swinging arm but rather at a point offset from the axis of the swinging arm. Still another object is to provide for rolling the club shaft about its axis during the swing from the top of the back swing to the end of the follow through, with the ability to easily adjust the initial position of the club about that axis.

These and other objects of the invention are achieved by a crank arm driven by a main drive shaft about the axis of a fixed gear thereby causing a secondary drive shaft supported in bearings at the free end of the crank arm to be rotated by a planetary gear meshed with the fixed gear and keyed to the secondary drive shaft. A block resiliently coupled to the secondary shaft carries a club swinging arm at a fixed distance from the axis of the secondary drive shaft such that as the crank arm is driven through an angle of less than 180° about the axis of the main drive shaft, the club swinging arm is driven through a greater angle (greater by about 180°) while the block is pivoted about the axis of the secondary drive shaft such that the effective length of the crank arm driving the club swinging arm varies between extremes by the fixed distance that the block spaces the club swinging arm from the axis of the secondary drive shaft. The block is positioned to displace the swinging arm relative to the axis of the main drive shaft through a predetermined arc, first in the direction of the back swing during the back swing and then in the other direction during the follow through after impact with a ball such that during the middle of the swinging motion of the arm, the block extends in a line from the crank arm as the golf club passes through the point of impact with a ball. The club is held at the free end of the swinging arm by gripping means that pivots freely about the axis of trunnions normal to the axis of the arm. The gripping means holds the club with its shaft axis offset below the axis of the swinging arm while the club head swings through the point of impact. The gripping means is supported by bearings in a barrel connected to the trunnions with its axis passing through the axis of the trunnions at 90° with the trunnion axis. A first beveled gear which turns on the axis of the barrel is keyed to the gripping means and engages a second beveled gear which turns on the trunnion axis. The second beveled gear is keyed to a worm gear employed to set the initial position of the club head through the beveled gears. Once the position of the club head is thus preset, the first beveled gear causes the gripping means to rotate the barrel and the club shaft through an angle of about 180° while the golf club pivots about the axis of the barrel trunnions as the arm is driven from the top of the back swing through to a stop at the end of a full swing.

DESCRIPTION OF THE PREFERRED EMBODIMENTS

Figure 1:
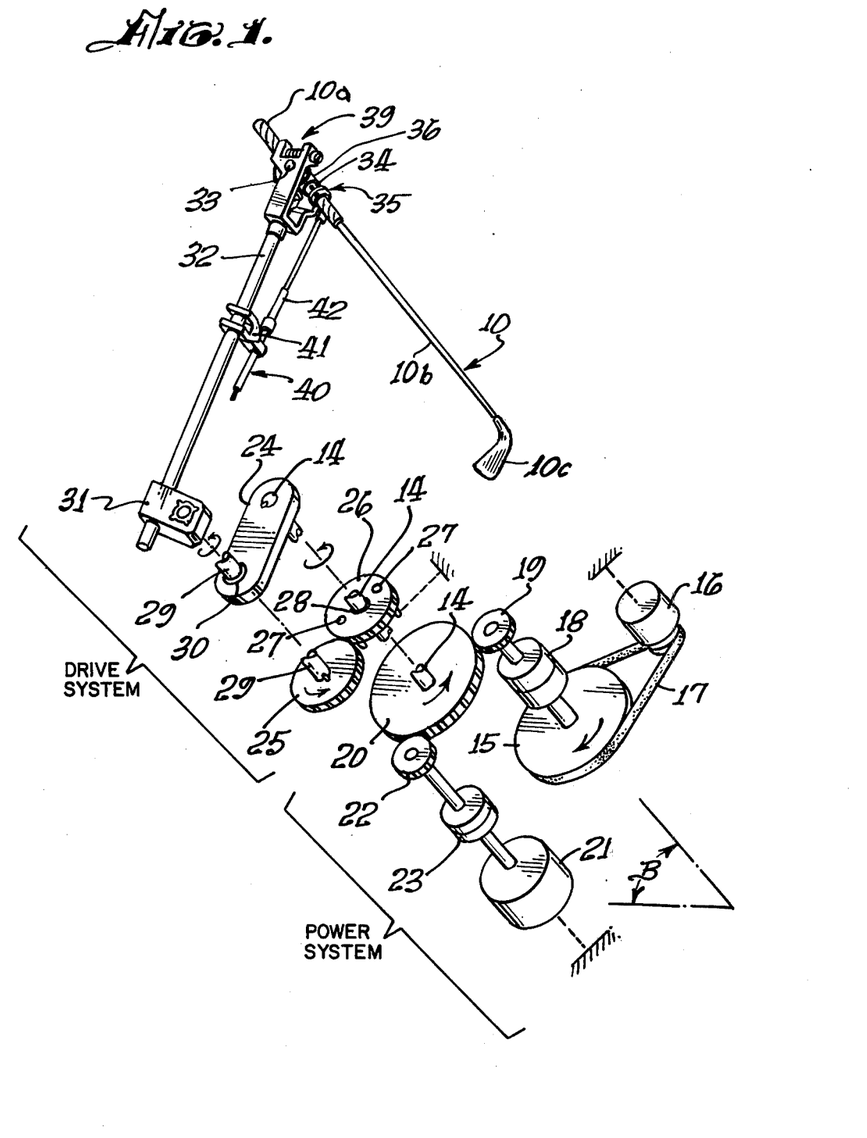
FIG. 1 is a diagrammatic illustration of an exemplary embodiment of the present invention.
Figures 2A, 2B:
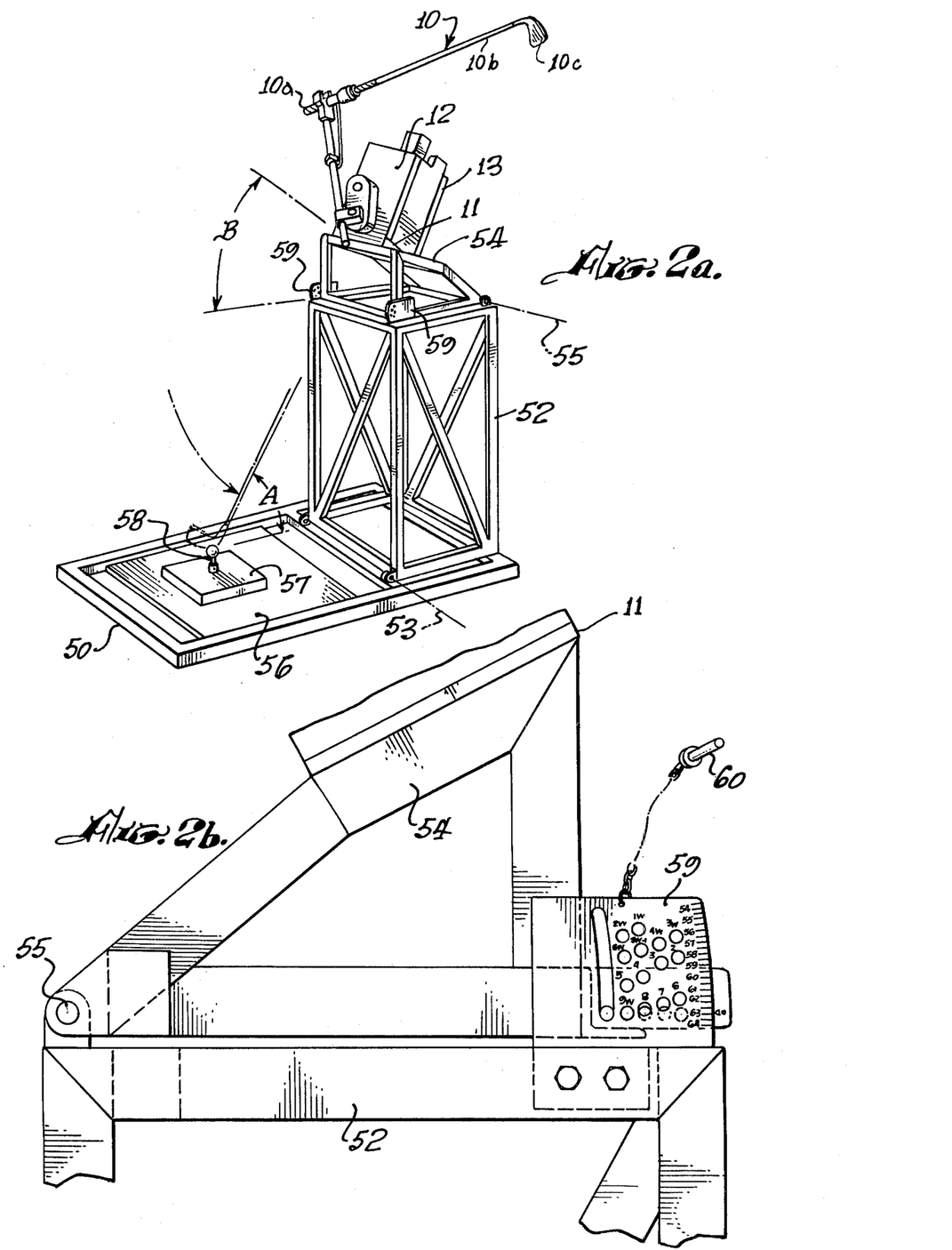
FIG. 2a is a perspective view of the apparatus of FIG. 1 housed in a structure that provides suitable support plates mounted on a collapsible stand.
FIG. 2b is an enlarged view of a portion of the stand showing how the lie angle for the apparatus is selected.

The golf club swinging apparatus of the present invention is illustrated schematically in FIG. 1. Only operative elements are included in the isometric view shown, it being understood that suitable base and support plates are provided to hold the apparatus in space for swinging a golf club 10 in a plane at an angle A with respect to the ground as shown in FIG. 2a. That angle is commonly referred to as the lie angle. When the tilt of the apparatus is properly adjusted to an angle B with respect to the ground, the lie angle A will be as prescribed for the golf club to impact a golf ball on the ground, or on a tee as shown in FIG. 2a. Only a base plate 11 and front and back support plates 12 and 13 are indicated by reference numerals in FIG. 2a, but in practice side plates and a top plate would be included to complete the housing for the power system.

Although a particular power system will be described by way of example, it is to be understood that the present invention is not limited to the use of that power system. Any system, such as a programmed servomechanism, may be used to drive a main shaft 14 which in turn drives the novel mechanism to which the present invention pertains.

The exemplary power system illustrated in FIG. 1 is comprised of a flywheel 15 driven to a desired speed by a motor 16 through a belt 17. An electromagnetically actuated slip (friction disc) clutch 18 disengages the flywheel from a drive pinion 19 until the flywheel has been brought to a desired speed. The clutch is then engaged to drive a gear 20 that is keyed to the main drive shaft 14. That in turn drives the mechanism of the present invention to swing the golf club 10 from the position shown in FIG. 1 at the top of the "back swing" through the position of FIG. 2a and around for a full "follow-through" after impact of a golf ball. Stops (not shown) limit the extent of the back swing and the follow-through. Also not shown in FIG. 1 is a hydraulic check member that absorbs the unexpended energy of the golf club after impact with a ball to bring the golf club to a smooth stop at the end of the follow-through.

The golf club swinging apparatus of the invention to be presently described is driven to the position shown in FIG. 1 by a motor 21 through a reverse drive pinion 22 engaging the main drive gear. A clutch 23 is employed to couple the drive motor 21 and the pinion 22 during that operation. When the pinion is not so coupled to the reverse drive motor, it turns freely with the main gear 20.

Referring now to the golf club swinging apparatus of the present invention, the main drive shaft 14 drives a crank arm 24 to cause a planetary gear 25 to be driven around a fixed gear 26. Bolts 27 secure the gear 26 in a fixed position to the forward support plate 12 (FIG. 2a), and a bearing 28 journals the main drive shaft in the axis of that fixed gear. A secondary drive shaft 29 journaled by a bearing 30 in the crank arm 24 is keyed to both the planetary gear 25 and a shoulder block 31 which secures an arm 32 as shown. The length of the arm 32 is arbitrary and may be adjusted in the block 31.

As the main drive shaft turns the crank arm 24, the planetary gear 25 causes the secondary drive shaft 29 to turn, thus driving the arm 32. The gear ratio between the fixed gear 26 and the planetary gear 25 is selected such that the secondary drive shaft 29 rotates to drive the arm 32 as the crank arm 24 is driven from the top of the back swing position shown in FIG. 3 through a position shown in FIG. 4 to the end position shown in FIG. 5. In that manner the crank arm 24 is driven through an angle C shown in FIG. 3 by the main shaft 14 while the arm 32 is driven through a greater angle by the secondary drive shaft 29.

Figure 7:
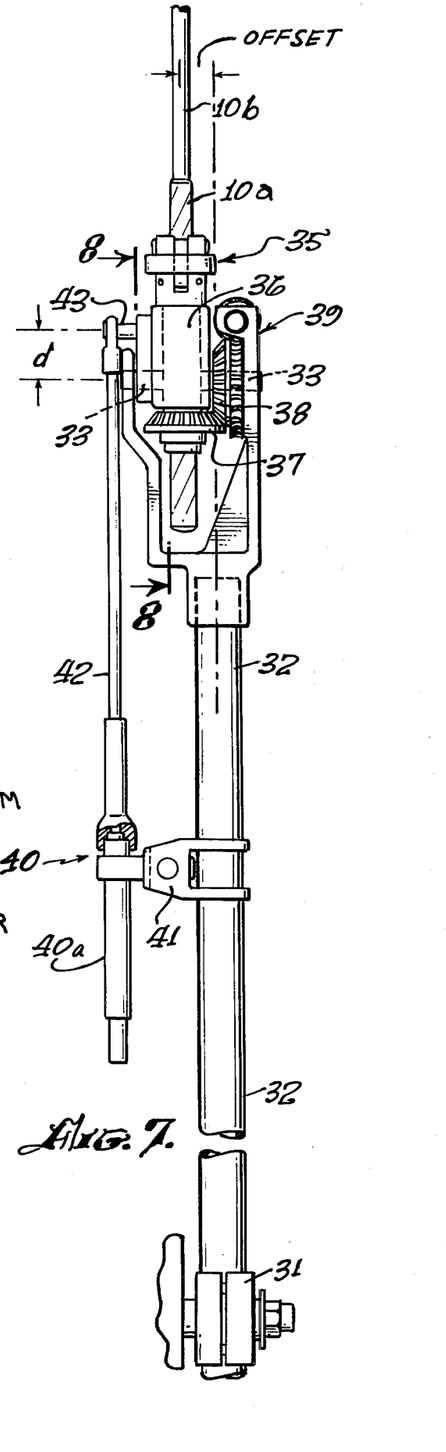
FIG. 7 illustrates details of construction of the end of a golf swinging arm in the apparatus of FIG. 1.
Figure 8:
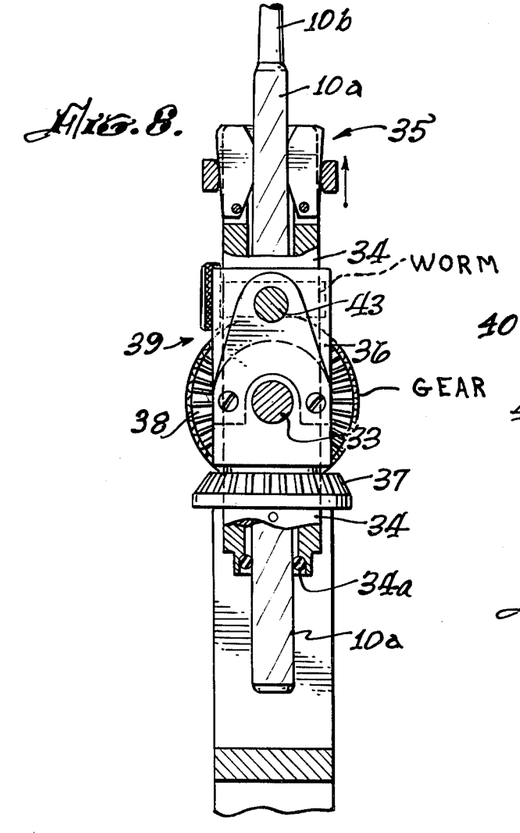
FIG. 8 is a sectional view taken on the line 8—8 of FIG. 7.

Trunnions 33 secured to a tubular gripping member 34 are supported by bearings in the free end of the arm 32. The length of the gripping member 34 is less than the length of the club grip 10a on a golf club shaft 10b. The tubular gripping member 34 is employed to so mount the golf club at the end of the arm 32 that the axis of the trunnions passes through the axis of the club grip at an intermediate point as shown in FIGS. 7 and 8. With the golf club in place, substantially all of its grip will be in the tubular member 34. Only the butt of the golf club grip protrudes from the rear end of the gripping member, and it may protrude as much as desired to adjust the pivot point up or down on the grip. A chuck-like means 35 at the front end of the gripping member secures the grip of the golf club. An O-ring 34a at the rear end of the gripping member 34 assures alignment of the grip axis with the axis of the gripping member.

Figure 3:
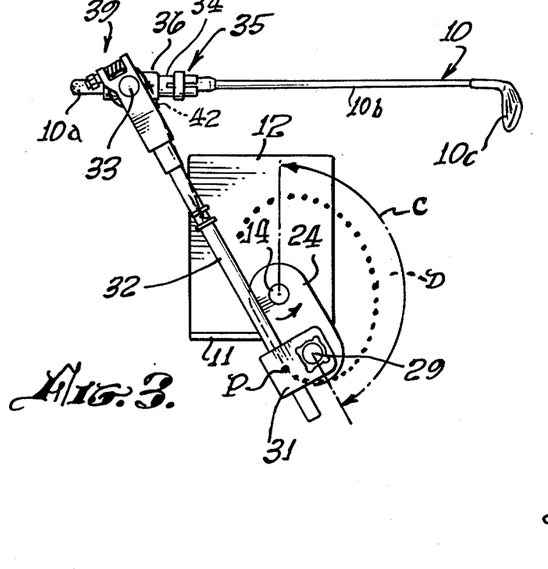
FIGS. 3, 4 and 5 are front views of the apparatus of FIG. 2 without the stand in three successive positions during a golf club swing starting in a back-swing position and ending in a follow-through position.
Figure 4:
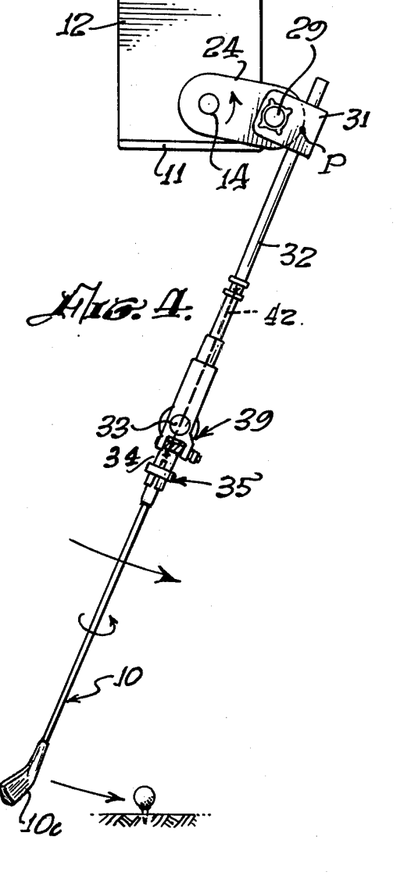
Figure 5:
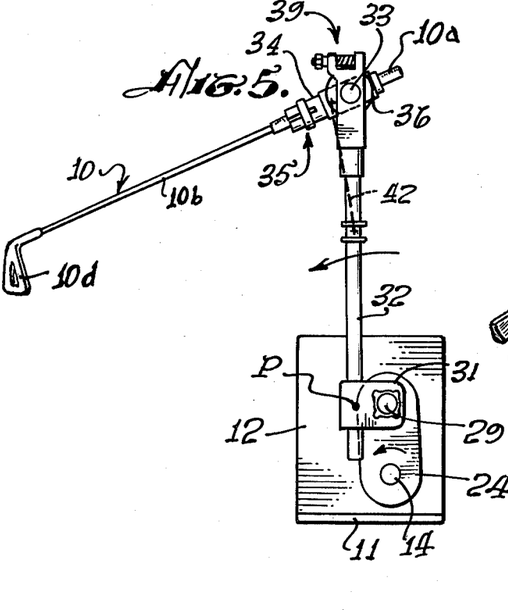

The pivotal action of the gripping member 34 about the trunnion axis simulates a golfer's wrist action and permits the club to swing freely into a substantially horizontal position at an acute angle with the arm 32 in the back swing shown in FIG. 3, then substantially in line with the arm 32 during the down swing, as shown in FIG. 4, and through to an end position shown in FIG. 5.

From FIGS. 3 through 5, it is evident that the striking face 10c of the golf club head is substantially parallel to the plane in which the club head is swinging at the beginning and end of the swing, but normal to that plane at the moment of impact with the ball. Consequently, as the arm 32 is cranked back by operation of the reverse drive motor 21 (FIG. 1) to the top of the back swing, the club head is rotated about 90° counter clockwise (as viewed by a right handed golfer) just like when the golfer cocks his wrists. In that position, the face of the club head is clearly visible by a person facing the golf club swinging apparatus as shown in FIG. 3. During the down swing, the shaft of the golf club is rotated clockwise through 180° to the position shown in FIG. 5 at the end of the swing with the rear of the club head 10d out.

To achieve this rolling action, the tubular gripping member 34 is so mounted inside a barrel 36 secured to the trunnions 33 that the gripping member 34 is free to rotate as the barrel 36 pivots on the trunnions. That rotation is produced by a beveled gear 37 secured to the gripping member 34 as shown in FIGS. 7 and 8. As the barrel 36 pivots about the axis of the trunnions, the beveled gear 37 "walks" around a secured beveled gear 38. The latter is secured in a selected position relative to the arm 32 by a worm gear 39. The worm gear permits rotating the beveled gear 38, and rotating the beveled gear permits rotating the tubular gripping member 34 through the beveled gear 37 to adjust the precise position desired for the face of the club head at the moment of impact with the ball. In testing golf clubs and balls, it is sometimes desirable to hit a ball with the face slightly "open" or "closed", i.e., rotated clockwise or counter clockwise as viewed by the golfer from a position precisely square with the direction of head motion at the moment of impact.

Figure 9:
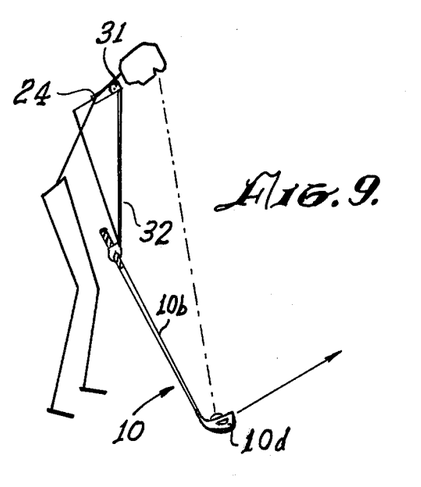
FIGS. 9, 10, 11 and 12 depict schematically a golfer in various positions during a golf swing to illustrate how the present invention simulates the motions of a golfer.
Figure 10:
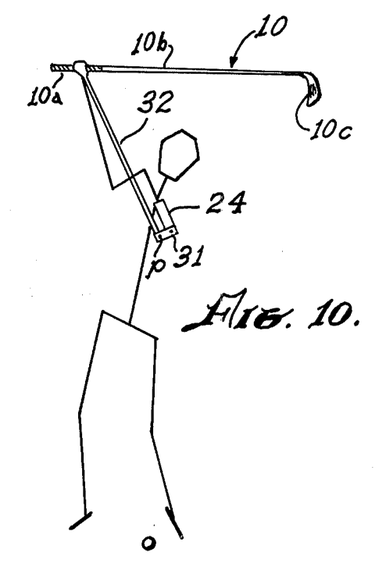
Figure 11:
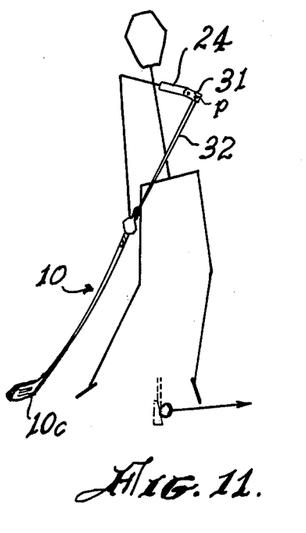
Figure 12:
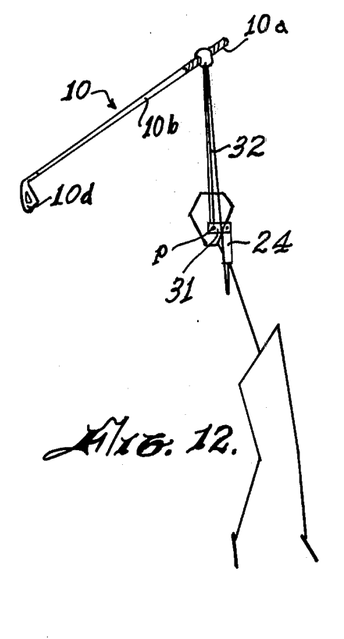

FIG. 9 depicts the general pattern of a full swing which may be likened to a spoked wheel with its axis at the center of a golfer's chest, but slightly in front. The axis of the main drive shaft 14 corresponds to that wheel axis. The crank arm 24 pivoted about the axis of the main drive shaft simulates the shoulder action of a right handed golfer depicted in FIG. 9. At the top of the back swing, the golfer's left shoulder is down and turned in as shown in FIG. 10. The shoulder point P swings out during the down swing, as shown in FIG. 11, and back in again at the top of the back swing as shown in FIG. 12. The block 31 simulates this shoulder action.

From the foregoing it is evident that the action of the block 31 moves the shoulder point P of this golf swinging apparatus down and in during the back swing, then back out during the down swing, and finally up and back in again during the follow-through part of the swing as the crank arm 24 is driven through an angle C illustrated in FIG. 3. FIGS. 10, 11 and 12 illustrate the positions of a golfer corresponding to the golf swinging apparatus in positions shown in respective FIGS. 3, 4 and 5. The crank arm thus causes the shoulder point to move through an arc D shown in FIG. 3 from the "shoulder down" position of the back swing (FIG. 3) to the "shoulder high" position at the end of the swing (FIG. 5). As the crank arm moves the block 31 through the angle C, and the block moves the shoulder point P back out and then in again during a full swing, the club swings out and pivots freely on the pinions in response to the centrifugal forces produced as the arm 32 is driven through a greater angle to the end position shown in FIG. 5. As the golf club pivots on the trunnions, the bevel gears 37 and 38 cause the shaft of the club to be rolled over through about 180°, thus simulating the wrist action of the golfer who rolls the golf club over as he uncocks his wrists from the back swing position, and cocks them again at the end of the stroke. All of this motion of the golf club is programmed and coordinated by the novel apparatus described. The apparatus only requires power for the main drive shaft to be driven in order for the apparatus to produce this motion.

The exemplary power system utilizes a flywheel as described with reference to FIG. 1. The power to be used in the golf swing is set by simply accelerating the flywheel to a predetermined speed (RPM) with the clutch 18 disengaged, and then engaging the clutch. All of the energy stored in the flywheel is then expended in driving the mechanism from the position shown in FIG. 3 to that shown in FIG. 5. The initial motion of the golf club is in a direction having a large vector parallel to the club shaft, and a small vector perpendicular to the club shaft. Consequently the initial acceleration will not cause undue flexing of the shaft. As the arm 32 continues, the vector normal to the shaft increases to swing the club head outwardly for a smooth and coordinated stroke. Initial acceleration of the arm 32, and thus the golf club 10, is controlled by the rate at which the clutch is engaged, as will be described more fully hereinafter.

Figure 6:
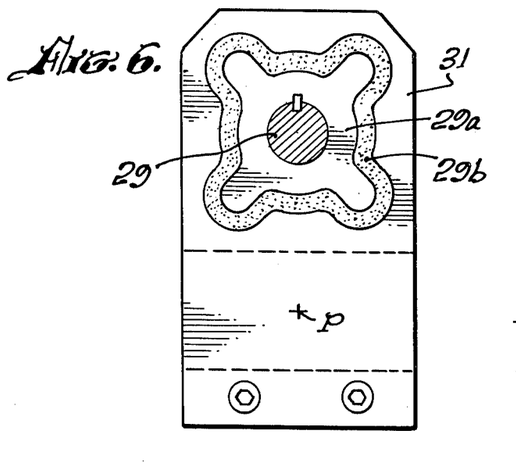
FIG. 6 illustrates details of a resilient coupling between the golf club swinging arm and a crank arm in the apparatus of FIG. 1.

To further assure smooth starting of the golf club motion, the shoulder block 31 is coupled to the secondary drive shaft 29 by a resilient coupling of a form shown by way of example in FIG. 6. The end of the shaft 29 is provided with a keyed or locked member 29a having four lobes. That member fits into an aperture in the block 31 of the same shape, but of larger dimensions. The space not taken up by the lobe member 29a is filled with resilient material 29b, such as polyurethane of a high density. During the initial torque, the lobes compress the material as motion of the swinging arm is started. Later, as the golf club swings out by centrifugal force, the energy stored in the compressed material is released. At the end of the swing, the arm is brought to a smooth stop in the position shown in FIG. 5 by hydraulic check means 40 shown in FIGS. 1 and 7. Any shock produced in the crank arm upon engaging the hydraulic check means near the end of the stroke is absorbed in the resilient material 29b.

Referring now to FIG. 7, a hydraulic cylinder 40a of the check means 40 is fastened to the arm 32 by a bracket 41. A rod 42 fastened at one end to a piston in the cylinder 40a is connected to a pin 43 protruding from the barrel 36 of the golf club gripping member 34 at some small distance d from the trunnions 33. As the golf club pivots about the trunnions 33, and begins to swing ahead of the arm 32 near the top of the follow-through, the rod 42 plunges the piston of the hydraulic check cylinder 40a in order to absorb the energy stored in the golf club and bring it to a smooth stop.

The cylinder of the hydraulic check means is filled with fluid which must pass through a limited passage from one side of the piston to the other as the piston moves in one direction. Consequently, the hydraulic check means is free at the beginning of the swing to assure that the golf club swings out smoothly from the position shown in FIG. 3 to that shown in FIG. 4.

It should be noted in FIG. 7 that the axis of the club gripping member 34 is offset below the axis of the arm 32, i.e., offset in a direction toward the ground as seen in FIG. 2. This is for the reason that a golf club gripped by the hands of the golfer is similarly offset from the wrist pivot.

Figure 13:
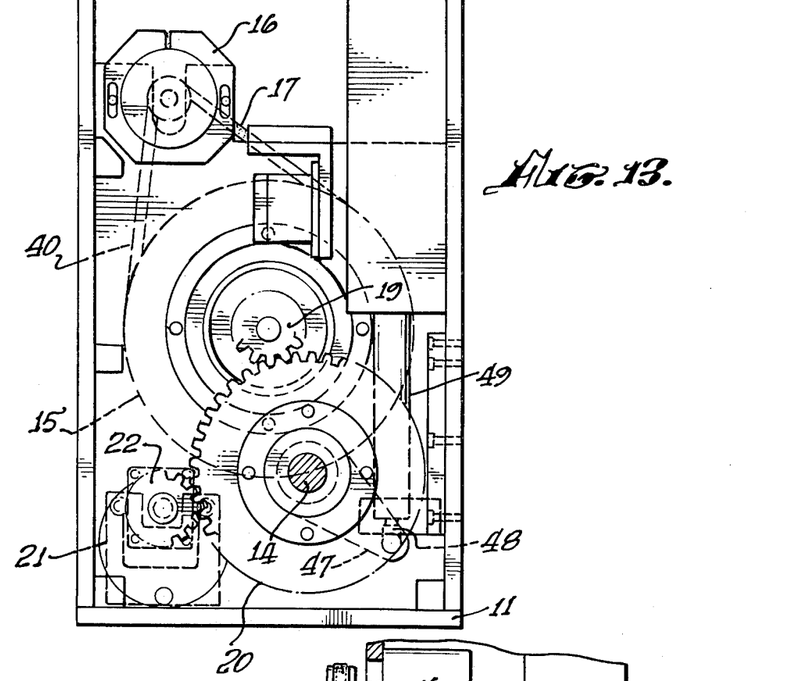
FIGS. 13 and 14 illustrate front and side views of an exemplary embodiment of the invention.
Figure 14:
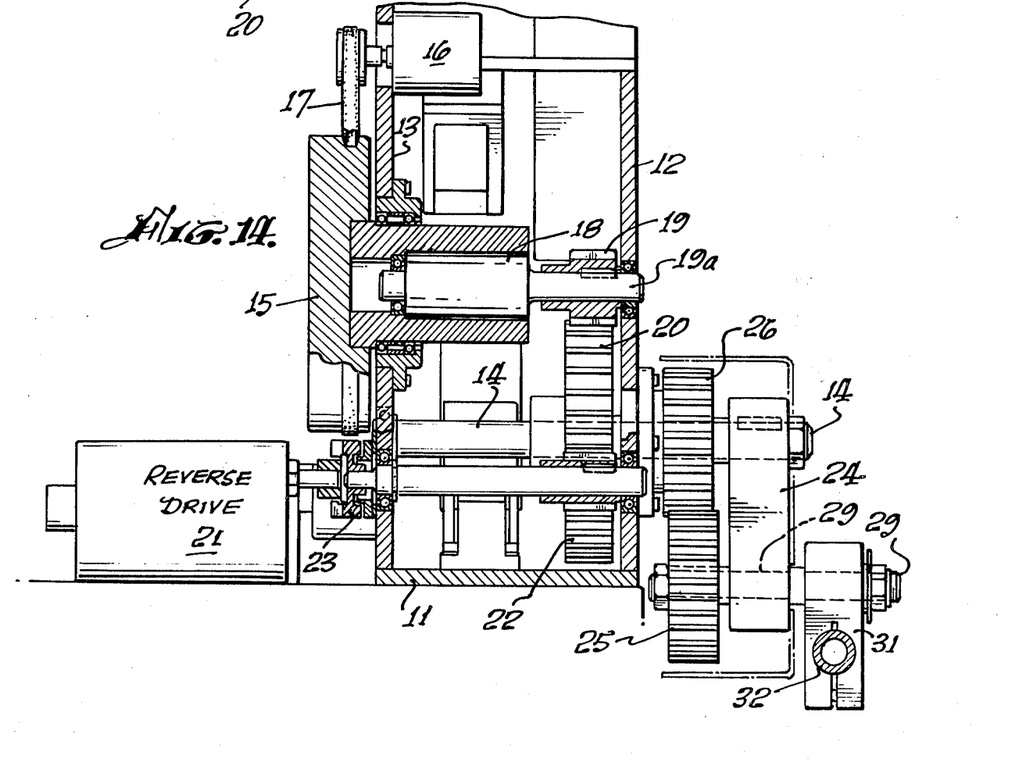

FIGS. 13 and 14 show front and side views of the exemplary power system. As noted hereinbefore with reference to FIG. 1, power to the main drive shaft 14 is delivered by the gear 20 coupled to the flywheel 15 through a clutch 18. When the clutch is engaged, the flywheel turns the pinion 19 to drive the gear 20. Before that is done, the flywheel is set into motion by the motor 16 through the belt 17 at an RPM appropriate for the desired energy to be expanded in swinging the golf club. A lever 47 (FIG. 13) keyed to the main drive shaft 14 swings down through an arc equal to that of the arm 32 from the position of FIG. 3 to the position of FIG. 5. As the lever 47 reaches the end of that arc, it engages a plunger 48 of a hydraulic check cylinder 49 to bring the arm 32 to a smooth stop.

As noted hereinbefore, the flywheel and clutch arrangement for delivering power to the main drive shaft 14 is disclosed by way of example and not by way of limitation. The only requirement of the present invention is that a predetermined amount of energy be delivered to the main drive shaft. In that regard, it should be noted that in the illustrated arrangement, the energy of the flywheel is not suddenly applied to the pinion 19 once the electromagnetic clutch 18 is engaged since the pressure plate will initially slip on the clutch disk. As current through the clutch coil increases, the slippage decreases and drive on the pinion 19 increases, as will be described more fully with reference to FIG. 15. That is desirable to avoid having an initial acceleration that is too high for the arm 32 and club 10.

Referring now to FIGS. 2a and 2b, there is illustrated a preferred stand for the mechanism of FIG. 1 comprising a base frame 50, which may be supported on wheels (not shown) that are locked once the stand is in place. An upright frame 52 is hinged on the base frame about an axis 53 to permit it to be folded forward for more compact storage while not in use or while being transported.

On top of the upright frame is a tilt table 54 hinged about an axis 55 to permit adjustment of its tilt, as will be more fully described, with reference to FIG. 6, and to permit it to be folded back over the upright frame 52 so that the upright frame can be folded forward as described hereinbefore.

Secured to the base frame is a tray 56 for a block 57. A tee 58 is secured to the block. The tray, and the position of the block on the tray, may be adjusted (by means not shown) to place the tee in the proper position for the golf club to be swung.

To secure the tilt table at different positions for the different clubs, plates 59 are provided with holes as shown in FIG. 2b. A scale on the forward edge of each plate indicates the lie angle A for the tilt angle B. When the table has been tilted to a proper lie angle for a particular club, such as the No. 3 iron, a hole in the frame of the tilt table will match the hole labeled "3" on the plate. A pin 60 is then inserted in the No. 3 hole to secure the tilt table in place. A pointer 61 will indicate on the scale the lie angle at which the table is secured.

A mechanism driven by an electrical or hydraulic motor may be employed to tilt the table to any desired lie angle, including angles for which pin locking holes are provided. If an angle is selected for which there is not a pin locking hole, the tilt drive mechanism itself will hold the table at the selected angle without the use of locking pins in holes.

Figure 15:
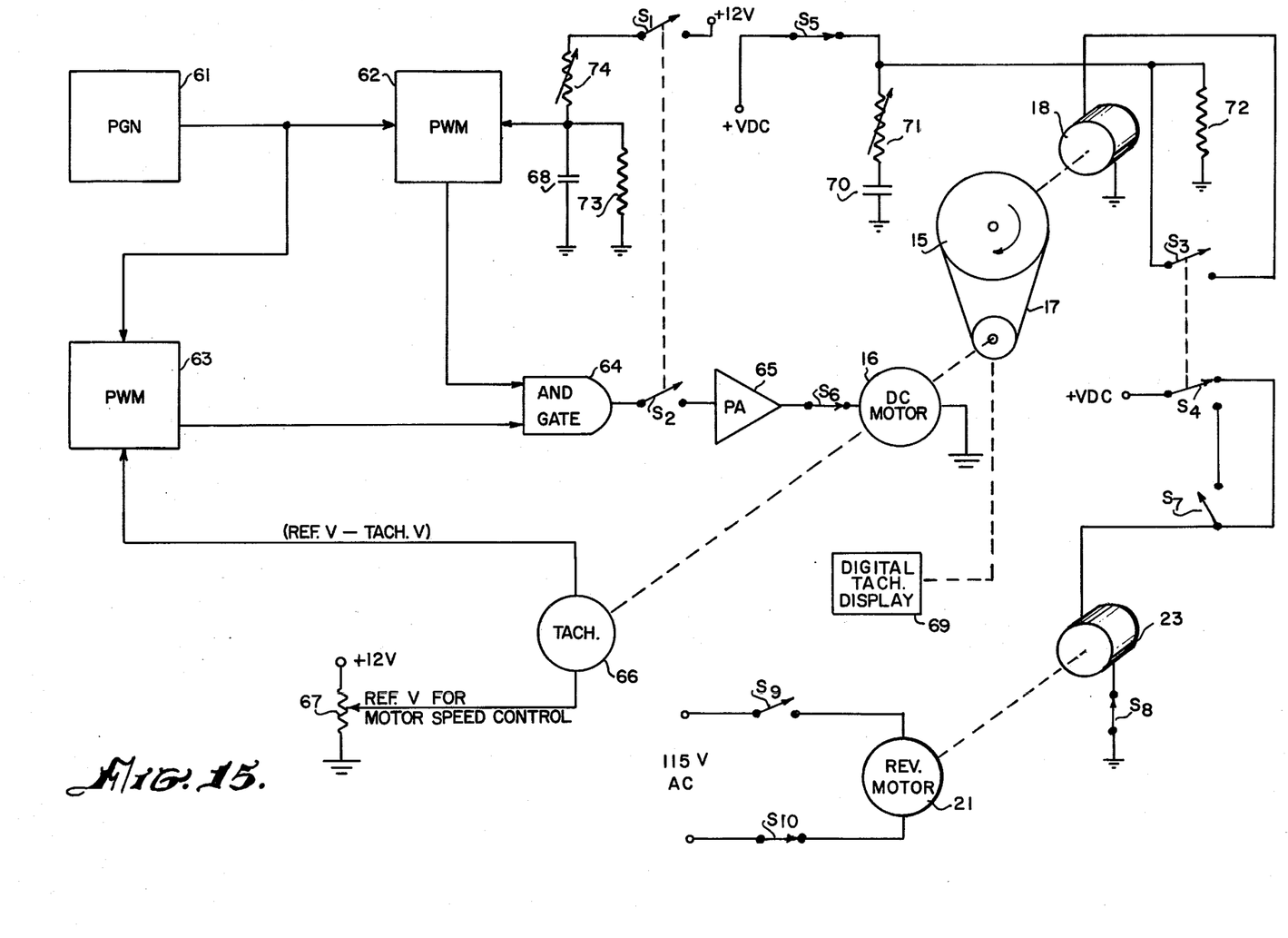
FIG. 15 is a schematic diagram of the electrical controls of the present invention.

Referring now to FIG. 15, a servo-loop for control of the motor 16 is comprised of a pulse generator (PGN) 61, a pair of pulse width modulators (PWM) 62 and 63, an AND gate 64, a power amplifier (PA) 65 and a tachometer 66 driven by the motor. A potentiometer 67 connected to a source of DC voltage (+V) is employed to establish a reference voltage (REF. V) for the motor speed desired. The tachometer is so connected in series between the potentiometer and the PWM 63 as to subtract from the reference voltage a voltage generated by the tachometer 66 proportional to motor speed. Initially the motor will be at rest, and the full reference voltage will be applied to the PWM 63 to cause pulses from the PGN to be transmitted to the AND gate 64 with a maximum duty cycle. At the same time, the PWM 62 receives a minimum (zero) reference voltage from a capacitor 68 to call for a minimum duty cycle. Under those conditions, the duty cycle of the pulses passed by the gate 64 are limited by the duty cycle of the PWM 62.

Once ganged switches $S_1$ and $S_2$ are closed to run the motor, the minimum transmitted by the gate 64 are coupled by the power amplifier 65 to the motor 16. The motor will then begin to turn the flywheel 15, and the tachometer 66 will begin to generate a voltage to decrease the duty cycle of pulses out of the PWM 63. At the same time, the capacitor 68 begins to charge to increase the reference voltage to the PWM 62 and increase the duty cycles of pulses transmitted by it to the gate 64, thus increasing the duty cycle of pulses to the power amplifier. In that manner the torque applied to the flywheel by the motor is gradually increased.

When the pulses from the PWM 62 reach a duty cycle greater than from the PWM 63, the power to the motor is limited by the duty cycle of pulses from the PWM 63 which gradually decreases as the tachometer voltage increases. Eventually the power applied to the load will decrease until a stable point is reached for the desired speed (RPM) of the flywheel set by the potentiometer 67. Any tendency for the flywheel to drop below the desired RPM due to friction will cause the tachometer voltage to decrease, and thereby cause the duty cycle of PWM 63 to increase. A digital tachometer display 68 indicates the RPM. The operator thus need only adjust the potentiometer 67 for the desired RPM to be employed. When that RPM is stable, a switch $S_3$ is closed to energize the electromagnetic clutch 18. Ganged with the switch $S_3$ is a single-pole, single-throw switch $S_4$ which provides current to engage the clutch 23 for the reverse motor 21 (FIG. 1) in order to hold the mechanism at the top of the back swing (FIG. 3).

A surge of current required to initially engage the clutch is provided by a capacitor 70 charged between runs through a normally closed switch $S_5$. That switch may be opened when the system is not in use, or may be omitted, in which case the on-off switch of the DC power supply may be turned off to keep the capacitor from being charged when the system is not in use. Once the capacitor 70 is discharged, a sustaining current is maintained for the clutch coil through the switch $S_5$. A potentiometer 71 controls the rate at which the capacitor discharges through the clutch coil and the peak amplitude of the initial surge of current. In that manner the rate at which the clutch engages can be set to provide control over the initial acceleration of the golf club swinging apparatus. Once the clutch is fully engaged, the flywheel is locked on the drive pinion 19 (FIG. 1) to transfer all of the remaining energy of the flywheel to the club.

At the end of the swing, the plunger 48 of the hydraulic check opens a switch $S_6$ and actuates a single-pole, single-throw, normally open switch $S_7$ to again engage the clutch 23. The clutch then functions as a brake to hold the mechanism at the top of the follow through (FIG. 5). A switch $S_8$ can be opened to release the brake in order to manually restore the mechanism to its initial position (FIG. 3), or the address position (FIG. 4), but instead a switch $S_9$ may be closed to engage the reverse motor to drive the mechanism back. At the top of the back swing (FIG. 3), a spring loaded stop switch $S_{10}$ is opened to disengage the reverse motor. Note that the golf club must be manually pivoted to the position shown in FIG. 3 after the mechanism has been driven to that position by the reverse drive motor.

Immediately upon completing a golf swing, the switch $S_3$ is opened to remove sustaining current from the clutch 18 and to allow the capacitor 70 to charge for the next run. Also the switch $S_1$ may be opened at the end of a swing to stop exercising the speed control loop until another swing is to be made. If there is not to be another swing, the switch $S_5$ is opened. A very large resistor 72 permits any residual charge in the capacitor 70 to be discharged when the switch $S_5$ is opened to turn the controls off. When there is to be another swing, opening the switch $S_3$ and closing the switches $S_1$ and $S_2$ again brings the flywheel 15 up to speed. A potentiometer 74 permits adjustment of the rate of which the flywheel is brought up to speed.

Although particular embodiments of the invention have been described and illustrated herein, it is recognized that modifications and equivalents may readily occur to those skilled in the art, such as the use of a programmed servomechanism in place of the flywheel to drive the novel mechanism, or in the case of using a flywheel, the motor speed control servo and the arrangement of control switches. In the novel mechanism itself, the length of the crank arm 24 and the length of the block 31 may be selected to simulate the swing of golfers of different builds (dimensions across the shoulders), and in the case of the block 31, the length selected may in fact be zero to simulate a golfer who does not turn his shoulder in during the back swing. Consequently, it is intended that the following claims be interpreted to encompass such modifications and equivalents.

I claim:

1. Apparatus for swinging a golf club to strike a golf ball for the purpose of testing the club or the ball, said club having a shaft with a grip at one end, said apparatus comprising a golf club swinging arm, a main drive shaft and means for driving said shaft through a predetermined angle with selected energy, a crank arm of selected length secured to said main drive shaft to be pivoted by said main drive shaft through said predetermined angle in a plane normal to said drive shaft, a fixed gear concentric with said main drive shaft, a secondary drive shaft parallel to said main drive shaft and supported by bearings at the free end of said crank arm, a planetary gear keyed to said secondary drive shaft and meshing with said fixed gear, means for securing said golf club swinging arm to said secondary drive shaft for driving said swinging arm through an angle greater than said predetermined angle and in an inclined plane normal to said secondary drive shaft, and pivotal means connected to the end of said club swinging arm securing said golf club at said grip to the end of said swinging arm.

2. Apparatus as defined in claim 1 wherein said means for securing a club swinging arm to said secondary drive shaft is comprised of a block having a selected length in a direction normal to said swinging arm for spacing said swinging arm from said secondary drive shaft a predetermined distance.

3. Apparatus as defined in claim 2 including means between said block and said secondary drive shaft for taking up and storing initial energy during a golf club swinging operation and for giving up energy stored during the swing.

4. Apparatus as defined in claim 1 wherein said pivotal means includes means for rotating a golf club about its shaft axis through a predetermined angle as said club is swung through said angle greater than said predetermined angle of said crank arm, and said rotating means includes means for presetting the rolled position of said club at the beginning of the swing.

5. Apparatus as defined in claim 4 wherein said means for securing a club swinging arm to said secondary drive shaft is comprised of a block having a selected length in a direction normal to said swinging arm for spacing said swinging arm from said secondary drive shaft a predetermined distance.

6. Apparatus as defined in claim 4 including means between said block and said secondary drive shaft for taking up and storing initial energy during a golf club swinging operation and for giving up energy stored during the swing.

7. Apparatus as defined in claim 1 wherein said pivotal means for securing said golf club to the end of said swinging arm secures said golf club for pivotal motion in a plane offset below the inclined plane of said swinging arm.

8. Apparatus as defined in claim 7 wherein said pivotal means is adapted to secure said golf club as a selected position on the grip of said golf club for pivotal motion about a selected point between the extreme ends of said grip.

9. Apparatus as defined in claim 1 including means for adjustment of the angle between said inclined plane of said swinging arm and a horizontal plane.

10. Apparatus as defined in claim 1 including means for damping the end of the pivotal motion of said pivotal means securing said golf club to the end of said swinging arm.

11. Apparatus as defined in claim 1 including means for damping the end of the pivotal motion of said crank arm at the end of said predetermined angle.

12. Apparatus as defined in claim 1 wherein said means for driving said shaft through a predetermined angle with selected energy is comprised of a flywheel, means for accelerating said flywheel to a desired speed of rotation for said selected energy, and clutch means for engaging said flywheel to said main drive shaft to swing said golf club.

* * * * *